United States Patent [19]

Haverstock

[11] 4,114,624
[45] Sep. 19, 1978

[54] SKIN CLOSURE MEANS
[76] Inventor: Charles B. Haverstock, 44 Frederick La., Glendale, Mo. 63122
[21] Appl. No.: 627,832
[22] Filed: Oct. 31, 1975

Related U.S. Application Data
[63] Continuation-in-part of Ser. No. 442,784, Feb. 15, 1974, Pat. No. 3,933,158.

[51] Int. Cl.² ............................................. A61B 17/08
[52] U.S. Cl. ..................................... 128/335; 83/821; 128/303 R
[58] Field of Search .............. 52/465, 469; 128/334 C, 128/335, 336, 305, 303, 132 R, 132 D; 24/201 C; 83/821; 33/174 G

[56] References Cited
U.S. PATENT DOCUMENTS

| 318,270 | 5/1885 | Lee | 52/469 |
|---|---|---|---|
| 741,362 | 10/1903 | Ohnstrand | 52/469 X |
| 1,428,495 | 9/1922 | Radcliffe | 128/335 |
| 2,371,978 | 3/1945 | Perham | 128/335 |
| 2,932,296 | 4/1960 | Sanders | 128/305 |
| 2,974,078 | 3/1961 | Petritz et al. | 52/465 X |
| 3,516,409 | 6/1970 | Howell | 128/335 |
| 3,568,276 | 3/1971 | Morgan | 128/335 X |
| 3,983,878 | 10/1976 | Kawchitch | 128/335 |

FOREIGN PATENT DOCUMENTS
215,065  5/1961  Australia .................................. 128/335

Primary Examiner—Robert W. Michell
Assistant Examiner—Michael H. Thaler
Attorney, Agent, or Firm—Charles B. Haverstock

[57] ABSTRACT

Improvements in skin closure means including means for uniting and holding separable closure members and skin portions attached thereto accurately together and to prevent separation thereof by forces which might otherwise cause the united members to separate. The subject construction also includes means for accurately guiding an instrument such as a scalpel while making an incision and for aligning and holding the separated edges of a skin wound or incision together during healing in such a way as to minimize or prevent the formation of scar tissue. The subject closure means are easy to apply quickly and accurately even under adverse conditions such as in first-aid treatment during emergencies, under disaster and wartime conditions, in emergency wards, in field, forest and wilderness situations and also under more controlled conditions such as operating rooms and doctors' offices particularly as the final step in completing a skin closure.

31 Claims, 11 Drawing Figures

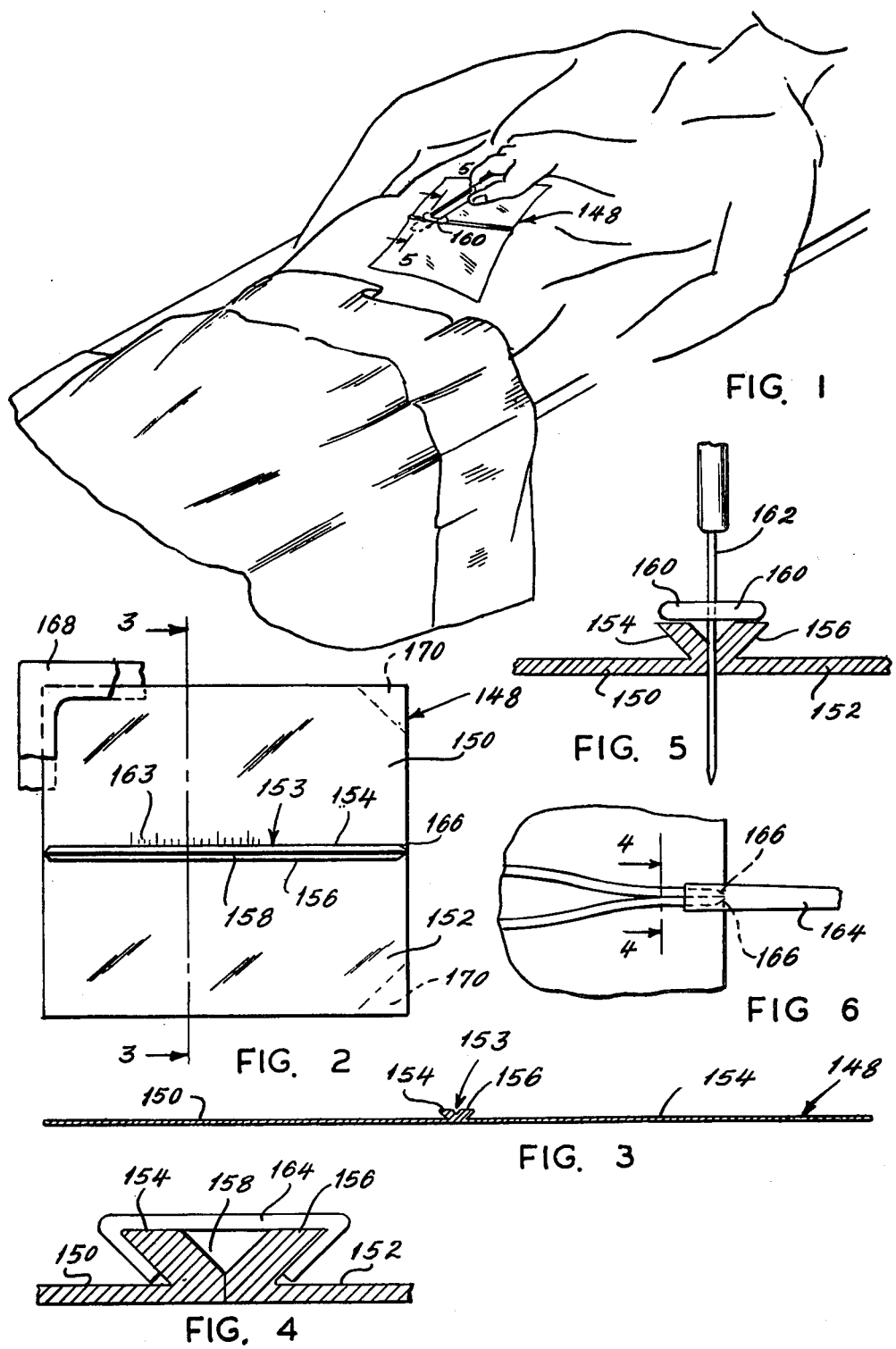

SKIN CLOSURE MEANS

This application is a continuation-in-part of copending U.S. patent application Ser. No. 442,784 filed Feb. 15, 1974, now U.S. Pat. No. 3,933,158 issued on Jan. 20, 1976 and entitled Skin Closure Means.

In my U.S. Pat. No. 3,863,640, issued Feb. 4, 1975 and copending U.S. application Ser. No. 442,784, filed Feb. 15, 1974, now U.S. Pat. No. 3,933,158, I disclosed various embodiments of skin closures by which the separated side edges of a skin injury, wound, incision, laceration or the like can be accurately aligned, closed and held after closure in the most advantageous position to facilitate healing with a minimum possibility for scar formation. Such devices are useful in situations where there is no access to medical assistance, and the prior constructions also have applications in surgical procedures as well as under emergency medical treatment procedures where time is limited and where other suturing means may be unavailable. The present means may even be superior to known forms of suturing in many cases. They are also useful in emergency situations such as in catastrophy and in wartime where there is a great need to be able to quickly and accurately close injuries or skin separations to prevent loss of blood and for other purposes readily apparent to those skilled in emergency treatment. Thus the present construction substantially reduces or eliminates the need for suturing and is also useful as a means of preventing the formation of scar tissue. It is recognized, however, that in some surgical procedures especially where deep incisions are made that some subcutaneous suturing may be desired, but even in these situations the ability to be able to quickly and accurately close the incision at the skin surface may be brought about by use of closure means such as disclosed in this, in my U.S. Pat. No. 3,863,640 and in my copending application Serial No. 442,784 now U.S. Pat. No. 3,933,158.

The present application covers several different embodiments of skin closure devices some of which are particularly adaptable for use in surgical procedures as a means to accurately guide the surgeon while he makes an incision and at the same time provides means for completing the final closure of the incision after the surgical procedure has been completed. Several different forms of the present devices are disclosed herein.

It is therefore a principal object of the present invention to provide means for accurately and quickly closing skin separations during surgical and other similar proceedings.

Another object is to improve the healing conditions between separated skin areas along a break or tear in the skin.

Another object is to reduce or eliminate the need for suturing particularly cutaneous suturing in medical-surgical procedures.

Another object is to minimize the formation of scar tissue and keloiding in the closing of incisions, lacerations and other skin separations.

Another object is to teach the construction of skin closure means which are adaptable to being made in any lengths and widths and which can be trimmed or cut to facilitate use as needed or desired depending on the nature, location and contour of the skin at the location where an incision is or is to be made.

Another object is to reduce the time required to perform surgical procedures which involve making incisions into flesh.

Another object is to teach the construction of a skin closure means which can be applied and closed without requiring any special tools.

Another object is to provide an effective skin closure which can be removed when it has served its purpose like an ordinary adhesive bandage.

Another object is to provide additional options for closing incisions in surgical procedures and the like.

Another object is to teach the construction and operation of a template which can be applied prior to surgery and which includes means which can be used to accurately reclose the skin separation at the conclusion of the surgical procedures.

Still another object is to provide means to accurately guide a surgical knife or scalpel during the making of an incision.

Yet another object is to provide means by which a surgeon can more carefully plan for and execute surgical procedures.

These and other objects and advantages of the present invention will become apparent after considering the following detailed specification which discloses several different embodiments of the subject construction in conjunction with the accompanying drawings wherein:

FIG. 1 is a view of a surgical template and a closure means constructed according to one embodiment of the present invention;

FIG. 2 is a top view of the device shown in FIG. 1;

FIG. 3 is a cross-sectional view taken on line 3—3 of FIG. 2;

FIG. 4 is an enlarged, fragmentary, cross-sectional view of the severable portion of the device of FIG. 3;

FIG. 5 is an enlarged, fragmentary, cross-sectional view taken on line 5—5 of FIG. 1;

FIG. 6 is an enlarged, fragmentary view similar to FIG. 2 showing the closure means therein being joined together by a closure member constructed according to the present invention;

Figure 7:
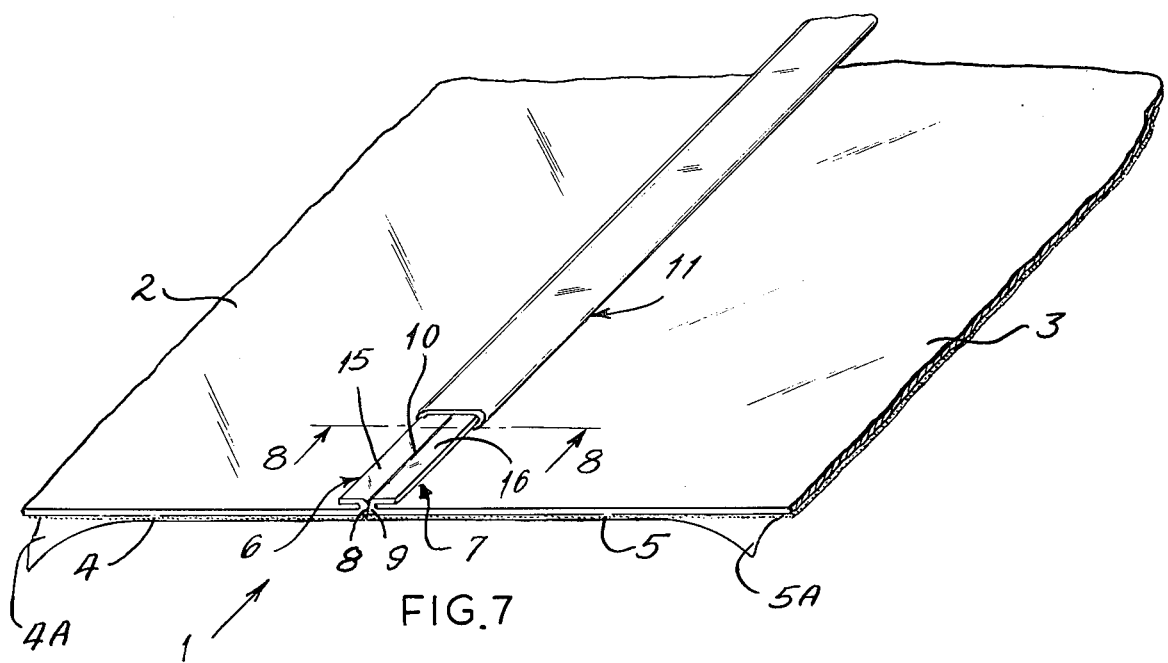
FIG. 7 is a perspective view of another embodiment of the subject closure means.

Referring to the drawings more particularly by reference numbers and wherein like numerals refer to like parts, number 148 in FIG. 1 indicates a surgical template constructed according to one embodiment of the subject invention. The embodiment 148 serves the dual functions of being a template which can be used by a surgeon during actual operation and as a final closure for the incision after the operation has been completed. The device 148 includes a relatively thin and preferably transparent plastic sheet which has two connected wall portions 150 and 152. The wall portions 150 and 152 have an adhesive on corresponding surfaces for attaching them to the skin at a location where the operation is to be performed, and a flanged track forming member 153 is attached to the portions 150 and 152 at an intermediate location on the opposite surface from the adhesive surface. The track forming member 153 is shown being formed by integral flanges 154 and 156. The flanges 154 and 156 as clearly shown in FIGS. 2, 4 and 5 are shaped so that together they form a V-shaped groove 158. Before being used the track 153 and the sheet portions 150 and 152 are preferably formed as parts of a one-piece construction which is adhesively attached to the body. The V-shaped groove 158 formed by the flanges 154 and 156 serves as a track for guiding a surgical knife or scalpel when making an incision during a surgical operation. It is therefore incumbent on the surgeon to accurately locate the subject means or template on the body prior to surgery so that the location and direction of the V-shaped groove 158 are in the position where the incision is to be made. After this is done, in order to make the incision, the surgeon simply places the cutting edge or point of the scalpel or other instrument in the groove 158 as shown in FIGS. 1 and 5 and presses down thereby severing the closure means at the location defined by the groove 158, and if desired, the depth of the incision can be accurately controlled by providing projection means such as the flanges 160 which are attached to the scalpel blade 162. The incision can extend the full distance across the subject template or even beyond, or it can extend for any portion thereof. This can be accurately determined by the surgeon by providing a dimension scale 163 along the flanges 154 and 156, and the template 148 can also have a pictorial or other representation and/or instructions drawn or otherwise applied thereto prior to or during surgery. The template can also have notes, directions or other information on it if desired, and the template including the portions 150, 152 and 153 can be perforated, if desired, to allow air to get to the skin for healing, comfort and other reasons. After the surgery has been completed, and after any required subcutaneous suturing has been performed, the final skin closure is completed by attaching a separate closure means 164 which may be similar to some of the closure means disclosed in this and my copending application Ser. No. 442,784. The closure means 164 can also be attached to one of the flanges 154 and 156 by any of the various means disclosed in my copending application, or it can be attached by sliding it longitudinally onto the severed flanges 154 and 156 starting at one end as clearly shown in FIG. 6. If the slide on method is used, it may be desirable to taper the ends of the flanges 154 and 156 as at 166 (FIGS. 2 and 6). This can be done at one or both opposite ends of the flanges to facilitate closing the skin by starting from either end. The subject device as well as the other embodiments can also be made to follow curved or other shaped incisions or skin separations as required in some types of surgery.

The sheet portions of the constructions disclosed herein are preferably made of relatively thin and flexible material such as sheet plastic so as to be able to easily and intimately conform to the skin. The flanges may also be plastic and may be integral with the sheet portions. The sheet portions are preferably though not necessarily transparent and the devices as stated may be perforated or made of porous material for the reasons given.

When any of the template constructions disclosed herein are made of thin flimsy plastic it is contemplated to position them in a frame prior to applying them to the skin in order to maintain them in a stretched and flat condition for ease of handling and so that they can be accurately located by the surgeon before actually being attached adhesively. For example, FIG. 2 shows the template embodiment 148 positioned in a relatively rigid frame 168. Thereafter, when the template is properly located where it is to be applied, and the protective cover layer on the adhesive has been removed, the central portion of the device 148 is pressed into adhesive attachment with the skin. Thereafter, the template can be accurately cut from the frame so that the attachment can be completed. This is done by cutting around the inner edges of the frame and thereafter pressing down the remaining unattached portions to firmly attach it to the skin. If desired, one or more corners or edge portions of the adhesive can be overlaid by a non-adhesive tab such as tab 170 to make it easy to get hold of the device for removal when it has served its purpose. The construction 148 as well as the other constructions including the flange portions thereof may be formed of many different kinds of materials including even being constructed of certain woven and non-woven materials such as are used in some surgical dressings.

Figure 8:
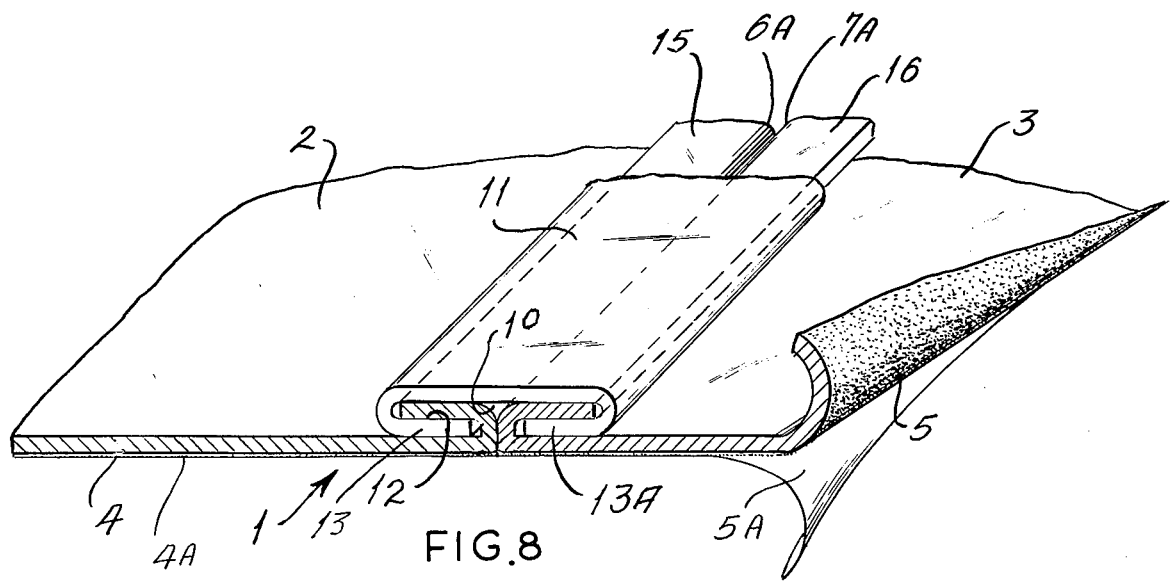
FIG. 8 is an enlarged, fragmentary, cross-sectional view taken on line 8—8 of FIG. 7.

FIGS. 7–8 show another embodiment 1 of the subject skin closure template means. The device 1 includes two separate relatively thin and preferably transparent plastic sheets 2 and 3. The sheets 2 and 3 have an adhesive means 4 and 5 on corresponding surfaces for attaching them to a skin or other item surface at a location where marking or cutting is to be effected. The adhesive layers 4 and 5 preferably extend over the entire skin contacting surfaces of the sheets 2 and 3. Elongated flanges 6 and 7 are attached to or made integral with the respective sheets 2 and 3 and form corresponding side edges thereof. The flanges 6 and 7 are preferably constructed to be somewhat harder or less flexible than the sheets 2 and 3 to which they are attached, and if desired, they can be made of the same or of a different material than the sheets, and preferably made so that they are not as easily cut but are preferably somewhat resilient and flexible. When applying the device to a skin surface or the like, the flanges 6 and 7 are placed with their respective surfaces 8 and 9 in abutment with one another as shown. When so positioned they define a normally closed slit-like passageway or groove 10 that extends between the two sheet portions 2 and 3. The flange portions 6 and 7, by being somewhat resilient, are able to bend or flex to assume a shape which will permit the passage therebetween of an instrument edge, such as a knife or scalpel edge or the point of a marking tool. The abutting surfaces 8 and 9 of the flanges are preferably also somewhat rounded especially on the sides thereof opposite from the adhesive layers to form a V-shaped groove so as to be able to better facilitate insertion of the scalpel and to more effectively guide the instrument edge during the making of an incision or other operation. The sides of the flanges that are adjacent to the skin, however, may be made to be more square shaped to bring the severed skin edges as close together as possible when reclosing the incision to minimize scar tissue formation. It is recognized, however, that it may be desirable to have some separation of the adhesive layers to permit entry of the scalpel blade and to allow for skin stretch.

The proper alignment of the sheets with respect to one another may be facilitated by the use of an elongated joining member 11 which is the member that is used to rejoin the sheets 2 and 3 at the conclusion of surgery. If this is done then the member 11 will be removed prior to or during the making of the incision. The member 11 is formed to define a channel 12 which is formed by spaced connected wall portions 13 and 13A that are constructed to engage and embrace the flanges 6 and 7. When the joining member 11 engages and embraces the flange portions 6 and 7 as shown in FIG. 8 the sheets 2 and 3 are properly aligned with respect to one another and are securely held together. In this condition, the construction is ready to be accurately positioned on the skin surface to be marked or cut both as to location and direction of the marking or cutting to occur, and should be adhesively attached. If the joining member 11 is used to facilitate alignment of the sheets 2 and 3 during attachment to the skin it should be removed prior to the marking or cutting, or it should be removed ahead of the cutting blade as indicated. As with the construction shown in FIGS. 1-6, a dimension scale, or pictorial or other representation, or instruction may be drawn on or otherwise applied to the embodiment 1 prior to or during the marking or cutting process, and as in the above construction the marking or incision may extend the full distance of the passageway 10 or even beyond, or it may extend any portion thereof.

If the construction 1 is employed during surgery, after the surgery is completed and any subcutaneous suturing which may be required is done, the final step is performed by sliding the joining member 11 onto the flanges 6 and 7 to rejoin and hold the sheets 2 and 3 and the attached skin surfaces together and in abutment. The joining member 11 may be constructed to be attached to the flange portions 6 and 7 in the way shown or it may be attached by any of the various means disclosed in my copending application Ser. No. 442,784, as well as by the means disclosed in FIGS. 1 and 6 herein. As with the construction of FIGS. 1-6 herein, if the slide on method is used, it may be desirable to taper one or both of the ends of the flanges 6 and 7.

Figure 9:
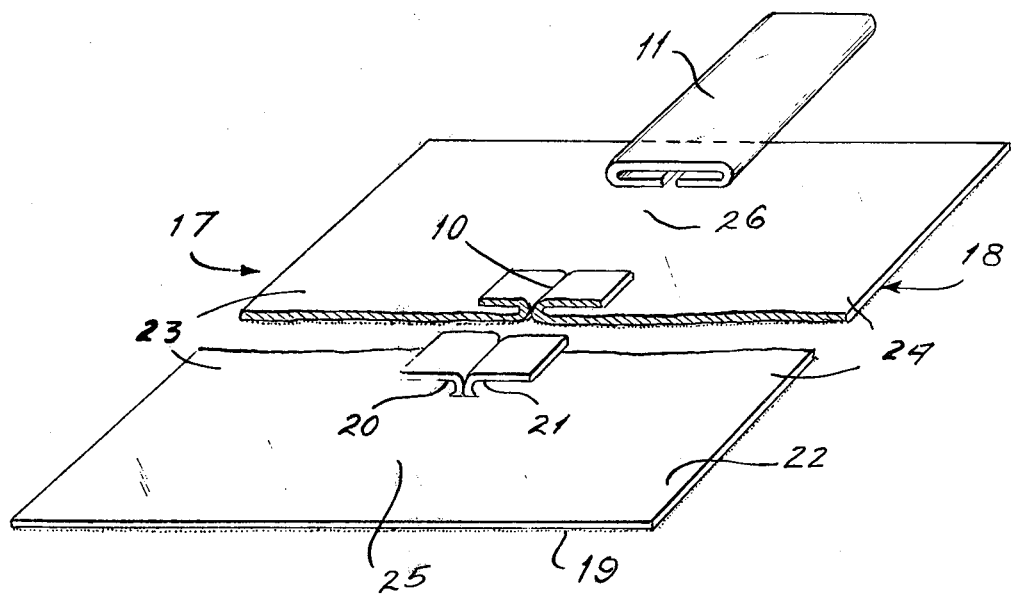
FIG. 9 is a perspective view of another embodiment of the subject skin closure means.
Figure 10:
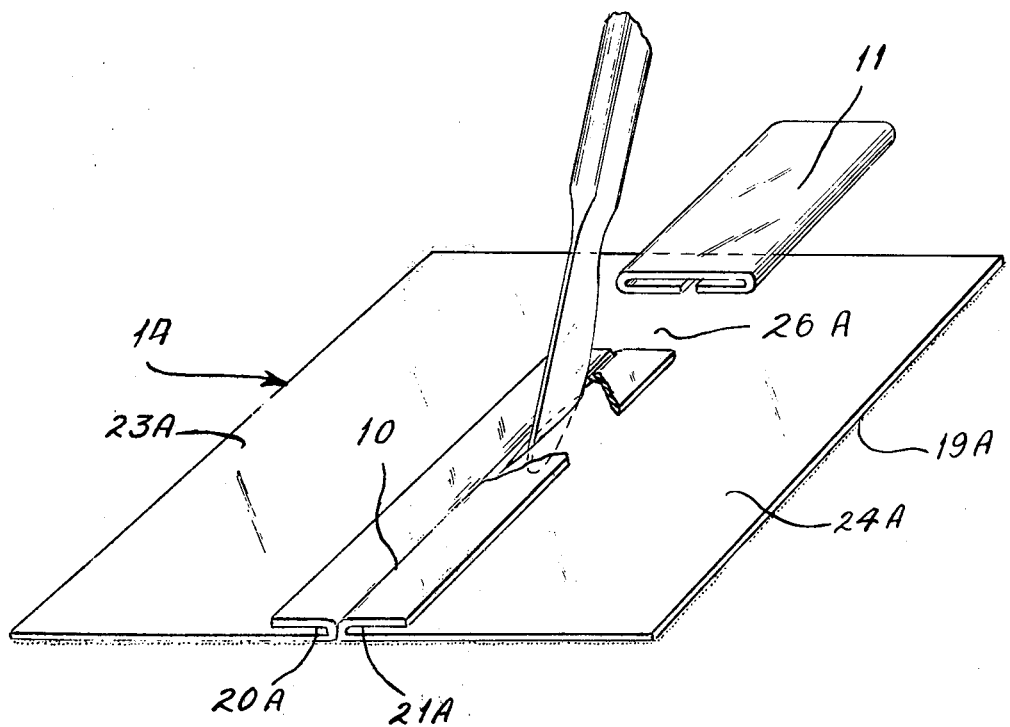
FIG. 10 is a perspective view of yet another embodiment of the subject skin closure means; and, FIG. 11 is a perspective view of still another embodiment of the subject closure means.

FIGS. 9 and 10 show other variations of the subject skin closure means. The device 17 in FIG. 9 includes a relatively thin and preferably transparent plastic sheet 18. The sheet 18 has an adhesive means on surface 19 thereof for attaching it to the skin surface at a location where the marking or cutting is to be effected. A pair of abutting flange portions 20 and 21 project from the sheet surface 22 at an intermediate location and the flanges extend less than the entire distance across the sheet 18, thus leaving sheet portions 23 and 24 which lie on opposite sides of the projecting flange portions 20 and 21 integrally connected by other sheet portions 25 and 26. The uses and purposes for the device 17 are similar to those described above.

FIG. 10 shows another variation in which there is an integral sheet connection 26A located at one end only of the flanges 20A and 21A, the opposite ends of the flanges extending to the sheet edge. FIG. 10 also shows a scalpel in position during the making of a surgical incision. This construction offers another option to the surgeon or to the person using the device to close a skin separation as where an injury has occurred. For example, the connected sheet portion 26A may make it easier to accurately attach the device and to hold the flap portions 23A and 24A in proper position prior to completing the skin closure.

Figure 11:
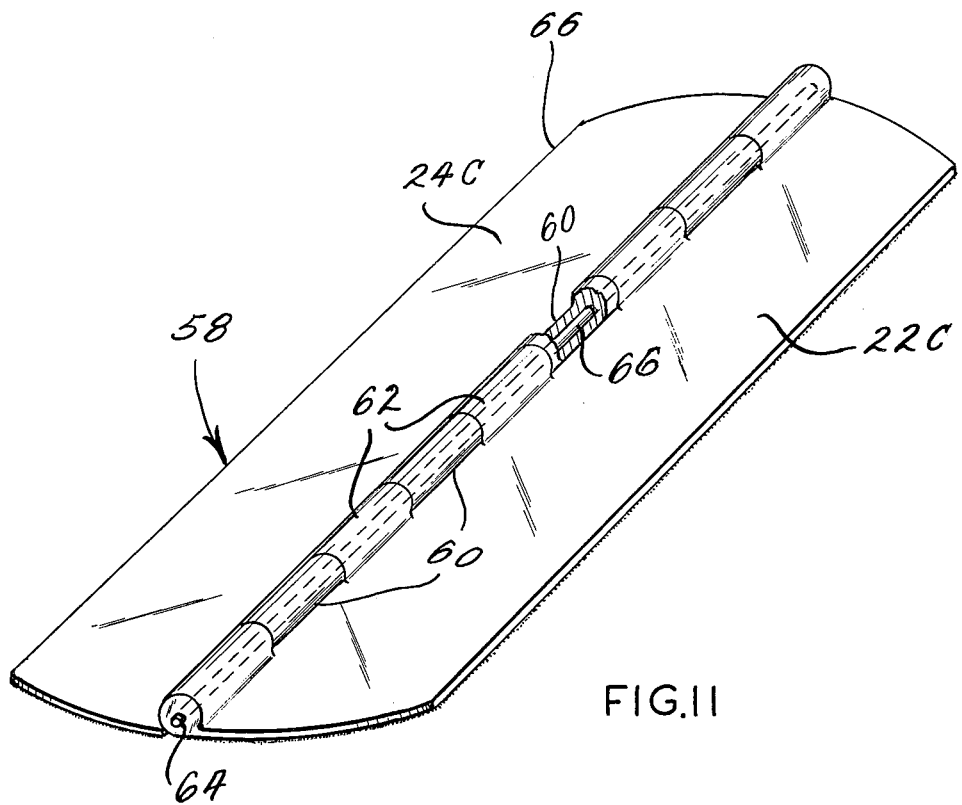

FIG. 11 shows another form of skin closure means 58 which may be used to close wounds, incisions or other skin separations. The construction of FIG. 11 can be used to join skin edges after the fact as in field and emergency situations or it can be used to close an incision by applying after the surgery is completed. Also if it is necessary or desirable for some reason to remove the template such as those disclosed above, a device such as the device 58 or any of the constructions disclosed in my previous cases for that matter can be used to reclose the skin separation. The closure means 58 includes two separable portions 22C and 24C preferably made of a relatively flexible material such as a plastic or plastic-like material, each member of which is constructed to be positioned having one side edge thereof extending along one side of the wound, incision, or other skin opening or separation to be closed. The two portions 22C and 24C each have adhesive means for attachment to the skin surface adjacent to the separated edges of the incision. The adhesive layers preferably extend over the entire skin contacting surfaces of the subject device although in some cases it may be desirable to have gauze or some other non-adhesive material in contact with certain portions of the skin area involved. When the portions 22C and 24C are applied to the separated edges of the skin there will usually be some space between them corresponding to the distance between the separated edges of the skin to be joined.

The portions 22C and 24C respectively have alternate interlocking tubular side edge portions 60 and 62 which may be made integral therewith. After being adhesively applied to the skin, the portions 22C and 24C are thereafter brought together by moving them to cooperating positions in which openings 64 through the portions 60 and 62 are in alignment. In this position a rod, a wire or a cord such as the rod 66 is threaded through all of the aligned openings 64 in a manner similar to inserting a hinge pin in a hinge assembly to hold the members together. The pin or cord 66 can thereafter be relatively easily removed to reopen the separation for inspection and/or medicating if desired. If a wire or cord is used for the member 66 it may have its ends extend from opposite ends of the tubular portions 60 and 62 and if desired the projecting ends can be twisted or tied to hold them together and in position as required. It is also contemplated with the construction 58 to keep the members 22C and 24C connected while it is being adhesively attached. If this is done the covering layer over the adhesive on one of the members only is removed, and that half of the device is applied along one side of the skin separation while the other portion is folded up and out of the way. After the first half is attached the adhesive covering on the other half is removed and the second half can be adhesively attached either by first separting it from the attached portion or while the members are hingedly connected.

Thus there has been shown and described novel skin closure means which in some cases also serve as means for guiding the edge of an instrument for marking or cutting into skin and for rejoining the skin separation. The constructions disclosed fulfill all of the objects and advantages sought therefor. It will be apparent from this description, however, that many other changes, modifications, variations and other uses and applications for the subject devices, in addition to those which have been disclosed, are possible and contemplated. All such changes, modifications, variations and other uses and applications which do not depart from the spirit and scope of the invention are deemed to be covered by the invention which is limited only by the claims which follow.

What is claimed is:

1. Means to close a skin separation by bringing together skin portions on opposite sides of the separation comprising a sheet member formed by a pair of sheet portions of relatively flexible material, each of said sheet portions being of one piece construction and having opposite surfaces, a layer of an adhesive on corresponding surfaces of each of said sheet portions for attaching the sheet portions to a skin surface at a location where separate skin portions are to be joined, each of said sheet portions having a side edge adapted to be located along respective sides of the skin separation, a flange on each of said sheet portions extending from and along the said side edge thereof, and means including a separate elongated wall member of uniform cross-section along its length extending along a substantial portion of said flanges and having a cross-sectional shape capable of embracing said flanges when the flanges are in abutment to maintain them and the respective sheet portions together and in abutment.

2. The means defined in claim 1 wherein the flanges and the respective sheet portions are integrally connected together, said connected flanges defining therebetween a groove along which a surgical instrument can be moved.

3. The means defined in claim 1 wherein the flanges are integral with the respective sheet portions to define a substantially closed slit therebetween when the flanges are in abutment.

4. The means defined in claim 1 wherein the elongated member has a cross-sectional contour shaped to conform to the cross-sectional shape of the flanges when the flanges are in abutment.

5. The means defined in claim 1 wherein the sheet member has a portion that extends beyond at least one end of the flanges for integrally uniting the sheet portions thereat.

6. The means defined in claim 1 wherein the flanges have opposite side edges, at least one side edge on each of said flanges extending along the side edge of the respective sheet portion.

7. A surgical template and closure means for attaching to skin portions comprising sheet portions of plastic-like material characterized by being able to intimately conform to a body skin surface, said sheet portions having opposite surfaces and side edges, means forming an adhesive layer on corresponding ones of the opposite surfaces of each of said sheet portions, elongated flange means attached to each of said sheet portions opposite from the adhesive layer and adjacent at least one side edge thereof, the flange means on said sheet portions when in abutment defining a groove extending therealong for receiving and guiding a cutting edge of an instrument used for making an incision wherein the cutting edge passes between the flange means, said flange means having spaced opposite side surfaces, and means including a separate channel-shaped wall member of uniform cross-section along its length having wall portions adapted to engage and embrace the flange means therealong to hold the flange means and the sheet portions together and in abutment.

8. The means defined in claim 7 wherein the flange means and the respective sheet portions are integrally connected.

9. The means defined in claim 7 wherein the elongated flange means have angularly related opposite side surfaces such that the portions of said surfaces adjacent to the sheet are closer together than other locations thereon.

10. The means defined in claim 7 wherein said sheet portions are formed of a transparent substance.

11. The means defined in claim 7 wherein means are provided to limit and control the depth of penetration of the cutting edge of the instrument, said means including the elongated flange means.

12. A surgical template and closure means comprising a sheet of plastic-like material characterized by being able to intimately conform to a body skin surface, said sheet having opposite surfaces, means forming an adhesive layer on one of said opposite surfaces, elongated track forming means on the other of said opposite surfaces of said sheet, said track being defined by similar connected flange portions shaped to form a groove extending therealong for receiving and guiding a cutting edge of a surgical instrument used for making an incision wherein the cutting edge severs the track forming means and the sheet at a location along the groove and enters the flesh, said track forming means after being severed having spaced opposed side surfaces, and means including a separate channel-shaped member of uniform cross-section along its length having wall portions adapted to engage and embrace the severed track forming means therealong to hold the severed portions and the adhesively attached skin portions together and in abutment.

13. The means defined in claim 12 wherein the elongated track forming means has angularly related opposite side surfaces such that the portions of said surfaces adjacent to the sheet are closer together than at other locations thereon.

14. The means defined in claim 12 wherein said sheet is formed of a transparent substance.

15. The means defined in claim 12 wherein means are provided to limit and control the depth of penetration of the surgical instrument, said means including the elongated track forming means.

16. Means to close skin separations during surgery comprising a sheet of relatively easily severable material, said sheet being selected to have a desired size and shape to accommodate the surgery to be performed and having opposed surfaces, an adhesive substance applied to one of said opposed surfaces for attaching the sheet to the skin at the location where surgery is to be performed, means on the opposite surface forming a track for guiding a surgical instrument during the making of an incision, said track forming means including an elongated strip of material attached to said opposite surface at an intermediate location thereon, said strip having an elongated groove formed therein for receiving the cutting edge portion of a surgical instrument which when pressed down to a desired depth and moved along the groove will sever the track forming means and the sheet and complete the surgical incision, and means cooperatively engageable with the severed portions of the track forming means when they are brought together into abutment at the conclusion of the surgery for holding the severed portions thereof and the severed portions of the sheet together, said means cooperatively engageable with the severed track forming means including a separate elongated channel shaped member of uniform cross-section along its length having side edge portions which engage the respective severed track forming portions to hold them together.

17. The means defined in claim 16 wherein the sheet is formed of a relatively transparent substance.

18. The means defined in claim 16 including means for holding and supporting the sheet in a relatively flat condition to facilitate the accurate positioning thereof before attaching it to the skin.

19. The means defined in claim 16 wherein the track forming means include an elongated member having angularly related opposite side surfaces located on opposite sides of the groove, said track forming means having a portion thereof adjacent to where it is attached to the sheet that is relatively narrower than other portions thereof.

20. The means to close skin separations defined in claim 16 wherein said elongated channel-shaped member is formed of a relatively stiff but somewhat flexible resilient material.

21. A means for guiding the edge of an instrument comprising a pair of relatively flexible sheet-like members each having opposite surfaces and a side edge, an adhesive layer on corresponding ones of said opposite surfaces of said members, and an uncovered, substantially continuous elongated flange integral with each of said members and extending along the side edge of each of said members, each of said flanges having a portion substantially perpendicular to the plane of the sheet-like member to which it is attached and a portion which extends from the distal end of said substantially perpendicular portion in a direction away from the respective sheet side edge, said flanges forming a normally closed slit therebetween extending completely between the pair of sheet like members along the flanges when the sheet-like members are positioned in side-by-side relationship with said substantially perpendicular flange portions substantially in abutment, said flanges being of sufficient rigidity to receive and guide an instrument therebetween.

22. The means defined in claim 21 including means cooperatively engageable with the flanges on said sheet-like members for joining and holding said sheet-like members together.

23. The means defined in claim 22 wherein the means cooperatively engageable with the flanges comprises an elongated channel-shaped member having wall portions adapted to be moved to a position embracing the flanges on said pair of sheet-like members to hold the sheet-like members together.

24. The means defined in claim 21 wherein said flange portions that extend away from the respective sheet side edges include portions that are in spaced parallel relation to the respective sheet-like members.

25. The means defined in claim 23 wherein the means cooperatively engageable with the flanges extend essentially the entire length of said flanges.

26. The means defined in claim 21 wherein said sheet-like members and the flanges thereon are made of a material that is relatively flexible and resilient.

27. The means defined in claim 21 wherein the flanges when positioned in abutment define a substantially V-shaped groove exposed on the opposite side of the flanges from the adhesive layers.

28. The means defined in claim 21 wherein the flange portions are relatively less flexible and more resilient than the sheet-like members to which they are attached.

29. Means for guiding the edge of an instrument comprising a relatively flexible sheet-like member having opposite surfaces, means forming an adhesive layer on one of said opposite surfaces, a pair of elongated uncovered, substantially continuous flange portions integral with and projecting from the other of said opposite surfaces, each of said flange portions having a surface which abuts a corresponding surface of said other flange portion, said abutting flange surfaces defining a substantially closed slit-like passageway extending therebetween, said passageway extending completely through said sheet-like member along the length of the flange portions, said flange portions being of sufficient rigidity to receive and guide an instrument inserted between said flange portions.

30. The means defined in claim 29 including means for cooperatively engaging and holding said pair of flange portions together and in abutment with one another.

31. The means defined in claim 30 wherein said engaging and holding means comprises an elongated channel-shaped member having wall portions adapted to engage and embrace said flange portions.

* * * * *